US 10,661,044 B2

(12) United States Patent
Hsiung et al.

(10) Patent No.: US 10,661,044 B2
(45) Date of Patent: May 26, 2020

(54) HUMIDIFICATION CHAMBER HAVING SUSPENSION TYPE FLOAT

(71) Applicant: NINGBO BESMED MEDICAL EQUIPMENT CORP., Zhejiang (CN)

(72) Inventors: Tao-Tsun Hsiung, New Taipei (TW); Xu-Xiang Wang, New Taipei (TW); I-Chen Tsai, New Taipei (TW)

(73) Assignee: NINGBO BESMED MEDICAL EQUIPMENT CORP., Zhejiang (CN)

( * ) Notice: Subject to any disclaimer, the term of this patent is extended or adjusted under 35 U.S.C. 154(b) by 305 days.

(21) Appl. No.: 15/726,918

(22) Filed: Oct. 6, 2017

(65) Prior Publication Data

US 2019/0046756 A1      Feb. 14, 2019

(30) Foreign Application Priority Data

Aug. 10, 2017    (TW) .............................. 106127095 A
Aug. 10, 2017    (TW) .............................. 106211831 U

(51) Int. Cl.
*A61M 16/16*         (2006.01)
*A61M 16/10*         (2006.01)
*F16K 31/22*         (2006.01)

(52) U.S. Cl.
CPC ........ *A61M 16/167* (2014.02); *A61M 16/109* (2014.02); *A61M 16/16* (2013.01); *F16K 31/22* (2013.01); *A61M 2205/3389* (2013.01)

(58) Field of Classification Search
CPC .. A61M 16/109; A61M 16/16; A61M 16/162; A61M 16/164; A61M 16/165;
(Continued)

(56) References Cited

U.S. PATENT DOCUMENTS 5,943,473 A * 8/1999 Levine ................ A61M 16/167
                                                                128/203.16
2007/0240767 A1* 10/2007 Rustad .................... F16K 31/20
                                                                137/430
(Continued)

FOREIGN PATENT DOCUMENTS

EP         2119466 A1 * 11/2009 .......... A61M 16/167
TW         363307 U  *  8/2009 ............ A61M 16/00

OTHER PUBLICATIONS

Machine translation of TW 363307 U (Year: 2009).*

*Primary Examiner* — Joseph D. Boecker
(74) *Attorney, Agent, or Firm* — Bacon & Thomas, PLLC

(57) ABSTRACT

A humidification chamber having suspension type float, the humidification chamber comprises a shell body, a water level control valve and a heated plate; the shell body has a water inlet, a gas inlet and a gas outlet; the water level control valve is provided with a position limiting element, a float and a sealing sheet; wherein the sealing sheet is disposed on a top end of the float, the heated plate is used for sealing the shell body to form a chamber space; when a liquid enters into the chamber space by a water inlet hole of the water inlet, the float will rise to comply with the water level increasing; when the sealing sheet contacts the water inlet hole of the water inlet, the sealing sheet can block the water inlet hole of the water inlet; when the water level of the chamber space is fell down, the position limiting element can prevent a bottom of the float from contacting the heated plate.

15 Claims, 21 Drawing Sheets

(58) Field of Classification Search
CPC ............... A61M 16/167; A61M 16/168; F24F 2006/008; F16K 31/18; F16K 31/20; F16K 31/22; Y10T 137/7358
See application file for complete search history.

(56) References Cited

U.S. PATENT DOCUMENTS

| | | | |
|---|---|---|---|
| 2010/0170511 A1* | 7/2010 | Payne ................. | A61M 16/167 128/204.14 |
| 2010/0171229 A1* | 7/2010 | Payne ................. | A61M 16/168 261/4 |

* cited by examiner

HUMIDIFICATION CHAMBER HAVING SUSPENSION TYPE FLOAT

BACKGROUND OF THE INVENTION

1. Field of the Invention

The present invention relates to a humidification chamber and more particularly to a humidification chamber having a water level control valve, the water level control valve is provided with a float. During the humidification process, the humidification chamber will consume a liquid which contained in the humidification chamber; when the liquid is added to the humidification chamber, the float will rise to comply with the water level increasing. The water level control valve can block a water inlet of the humidification chamber, therefore the water level control valve can control the water level of the humidification chamber.

2. Description of Related Art

A prior-art is disclosed in U.S. Pat. No. 7,722,016 (its patent family has Australia Patent No. AU2007290261B2, European Patent No. EP2056912A1, Japan Patent No. JP5398868B2, PCT Patent No. WO2008027670A1), the prior-art disclosed a humidification chamber, the humidification chamber has a float, the float has a seal element which is movable into and out of a valve seat; when the water level of the humidification chamber exceeds a first level, the seal element will seal off a water inlet; when the water level of the humidification chamber is below the first level, the seal element will open the water inlet; the float has a stand-off rib to prevent the lower end of the float from contacting a heat conductive plate.

The stand-off rib of the float may still be in contact with the heat conductive plate when the water level of the humidification chamber is too low. Moreover, the stand-off rib of the float may still be in contact with the heat conductive plate when the water inlet does not replenish water into the humidification chamber (e.g., a water storage container connected to the water inlet has no water). Thus, the prior-art still requires improvement.

SUMMARY OF THE INVENTION

It is therefore an object of the invention to provide a humidification chamber having suspension type float, the humidification chamber comprises a shell body, a water level control valve and a heated plate; the shell body has a water inlet, a gas inlet and a gas outlet; the water level control valve is provided with a position limiting element, a float and a sealing sheet; wherein the sealing sheet is disposed on a top end of the float, the heated plate is used for sealing the shell body to form a chamber space; when a liquid enters into the chamber space by a water inlet hole of the water inlet, the float will rise to comply with the water level increasing; when the sealing sheet contacts the water inlet hole of the water inlet, the sealing sheet can block the water inlet hole of the water inlet; when the water level of the chamber space is fell down, the position limiting element can prevent a bottom of the float from contacting the heated plate.

It is therefore another object of the invention to provide a humidification chamber having suspension type float, the humidification chamber comprises a shell body, a position limiting element, a float and a heated plate; the shell body has a water inlet, a gas inlet and a gas outlet; an inside of the water inlet has an extending tube, an inner wall of the extending tube has a plurality of guiding ribs; the position limiting element has a through hole and an inner edge, the inner edge has at least one notch; an extending portion of the float has at least one hook, a top end of the extending portion is provided with a sealing sheet; the heated plate is used for sealing the shell body to form a chamber space; wherein the extending portion can pass through the through hole, the hook can pass through the notch, and the float can be rotated to an angle, therefore the hook can be located at an inside of the inner edge; the position limiting element is configured to be fixed on the extending tube, therefore the hook and the notch can be separated by the guiding ribs.

First advantages of the invention include the float can be suspended on the position limiting element when liquid replenishment of the chamber space is not enough, that will form a distance between the heated plate and the bottom of the float. When the chamber space has no liquid at all, the bottom of the float still does not contact the heated plate.

Second advantages of the invention include the top end of the float is provided with at least one pressure released vent, the sealing sheet is appressed on the top end of the float, and the pressure released vent is configured to be closed by the sealing sheet, therefore the sealing sheet can prevent the liquid from infiltrating into the float. When the liquid is heated by the heated plate, the expansion pressure of the float will be released from the pressure released vent.

Third advantages of the invention include the inner edge of the position limiting element has at least one notch, the notch is helpful to the liquid to enter into the chamber space when the water inlet hole of the water inlet inputs the liquid.

The above and other objects, features and advantages of the invention will become apparent from the following detailed description taken with the accompanying drawings.

DETAILED DESCRIPTION OF THE INVENTION

Figure 1:
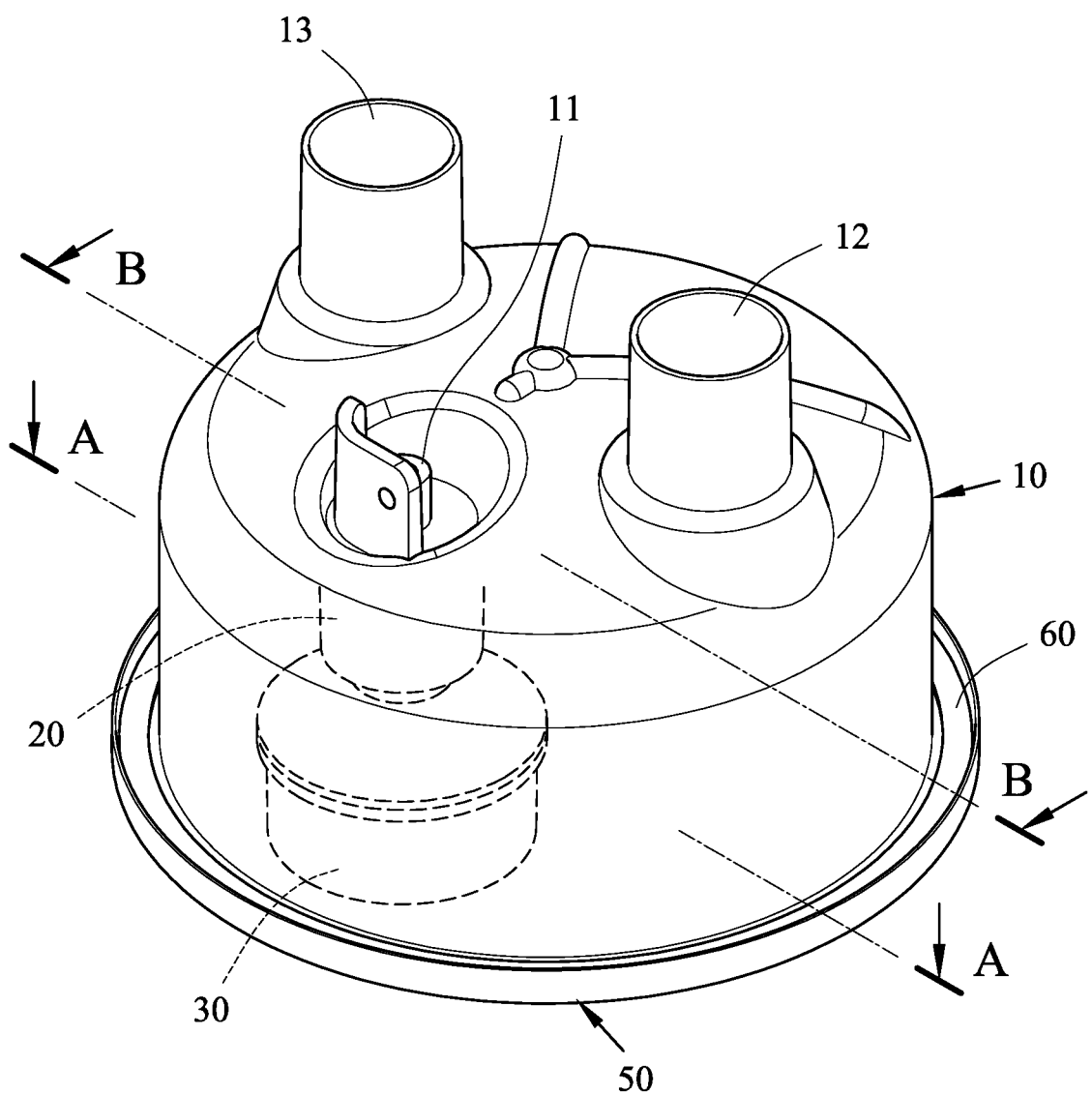
FIG. 1 is a perspective view showing a first preferred embodiment of the invention.
Figure 2:
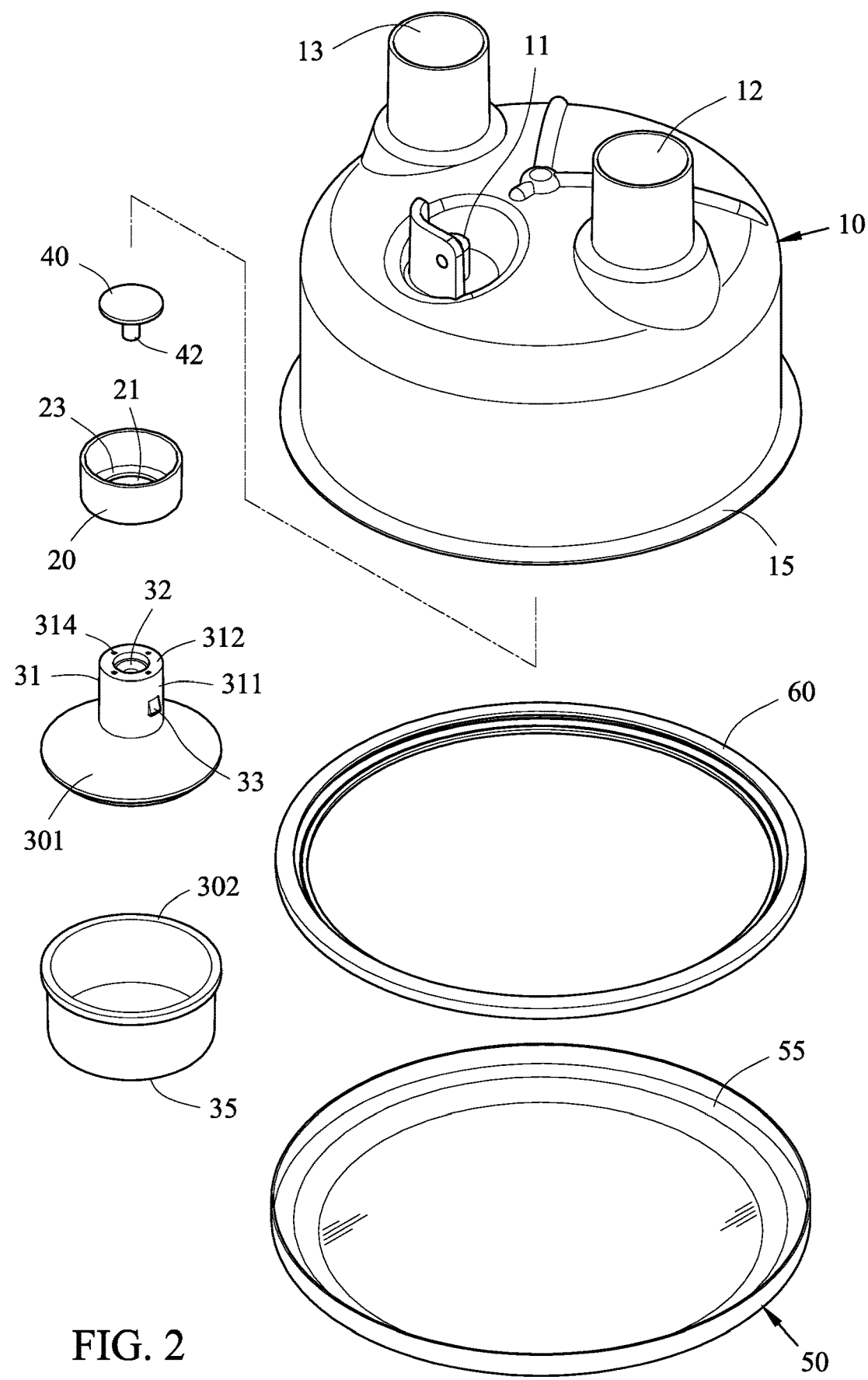
FIG. 2 is an exploded view showing the first preferred embodiment of the invention.
Figure 3:
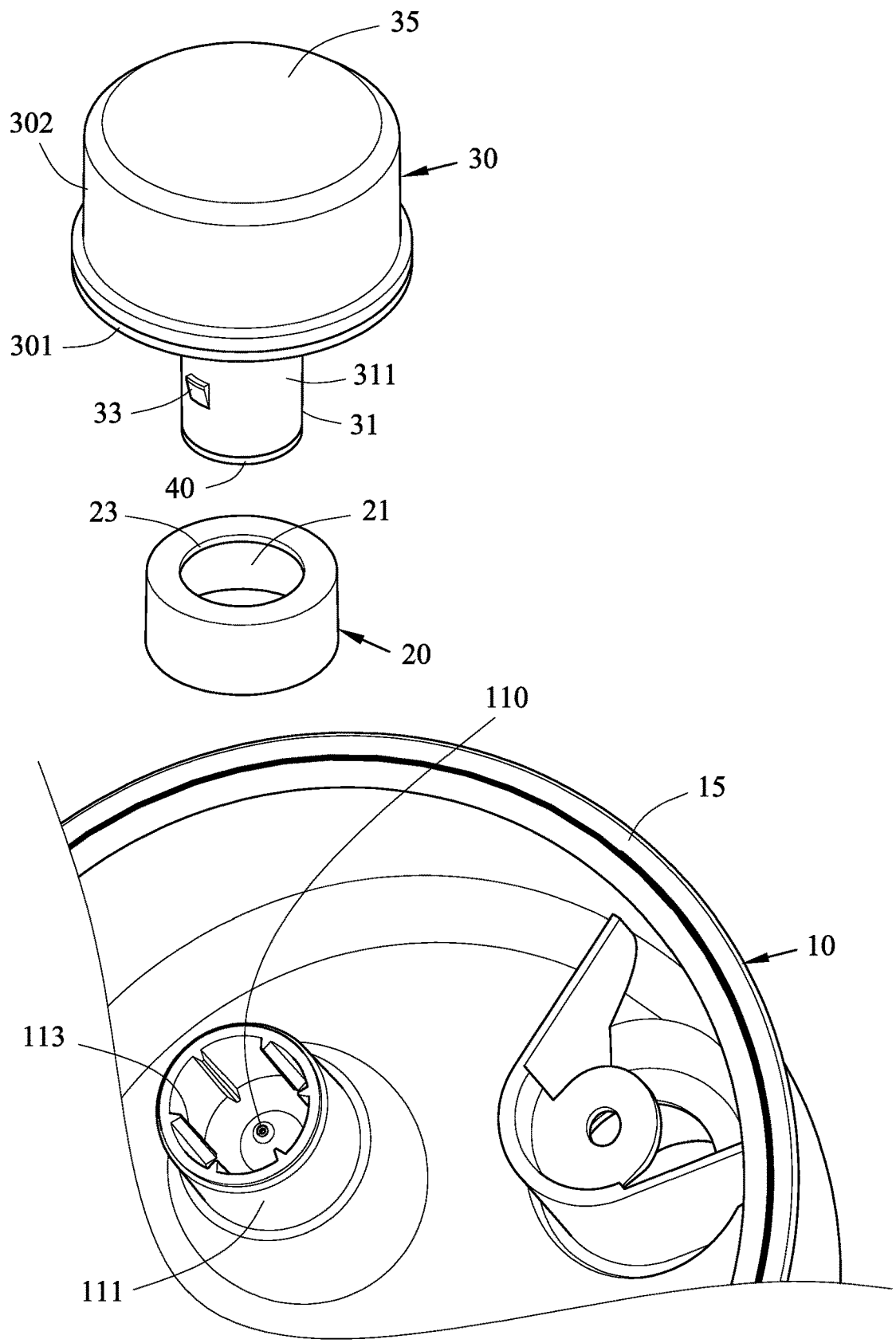
FIG. 3 is a partial exploded view showing the first preferred embodiment of the invention.
Figure 4:
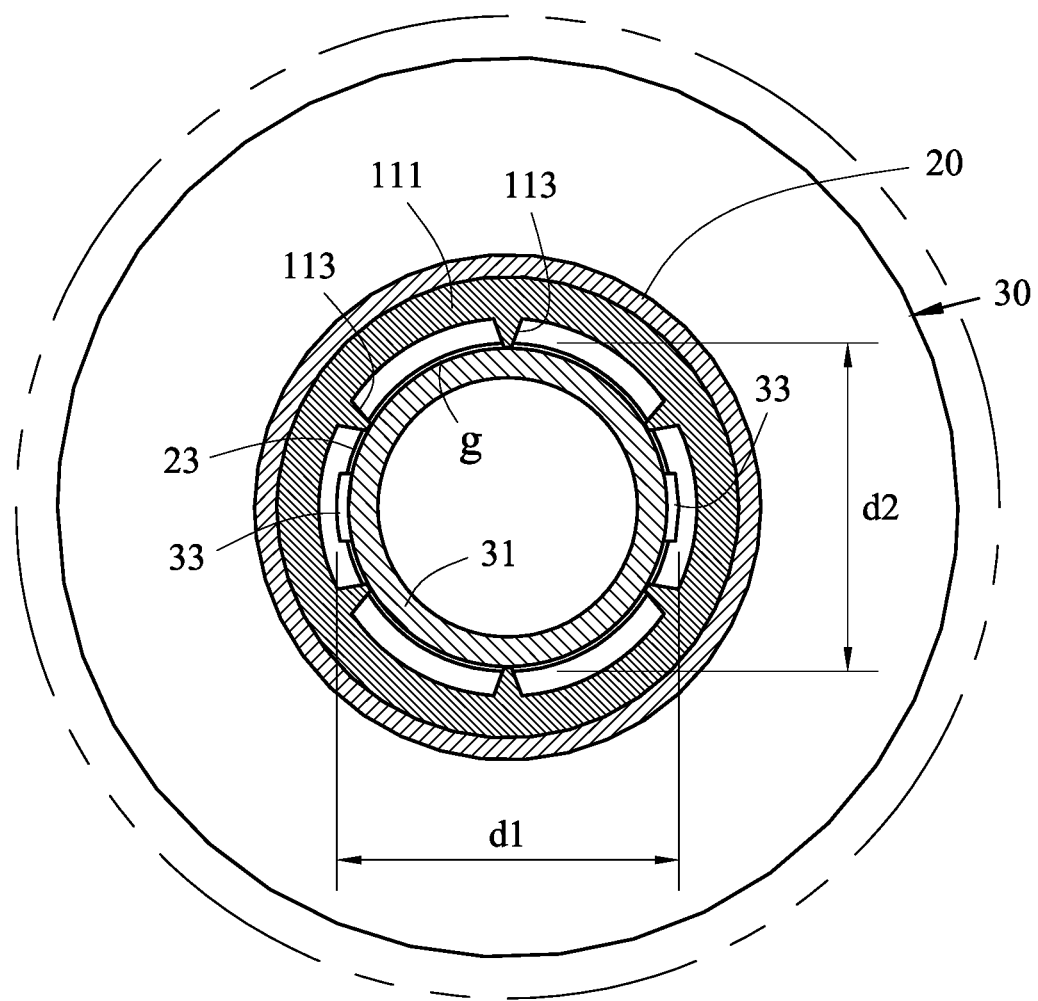
FIG. 4 is a partial cross-sectional perspective view along a line A-A of FIG. 1.
Figure 5:
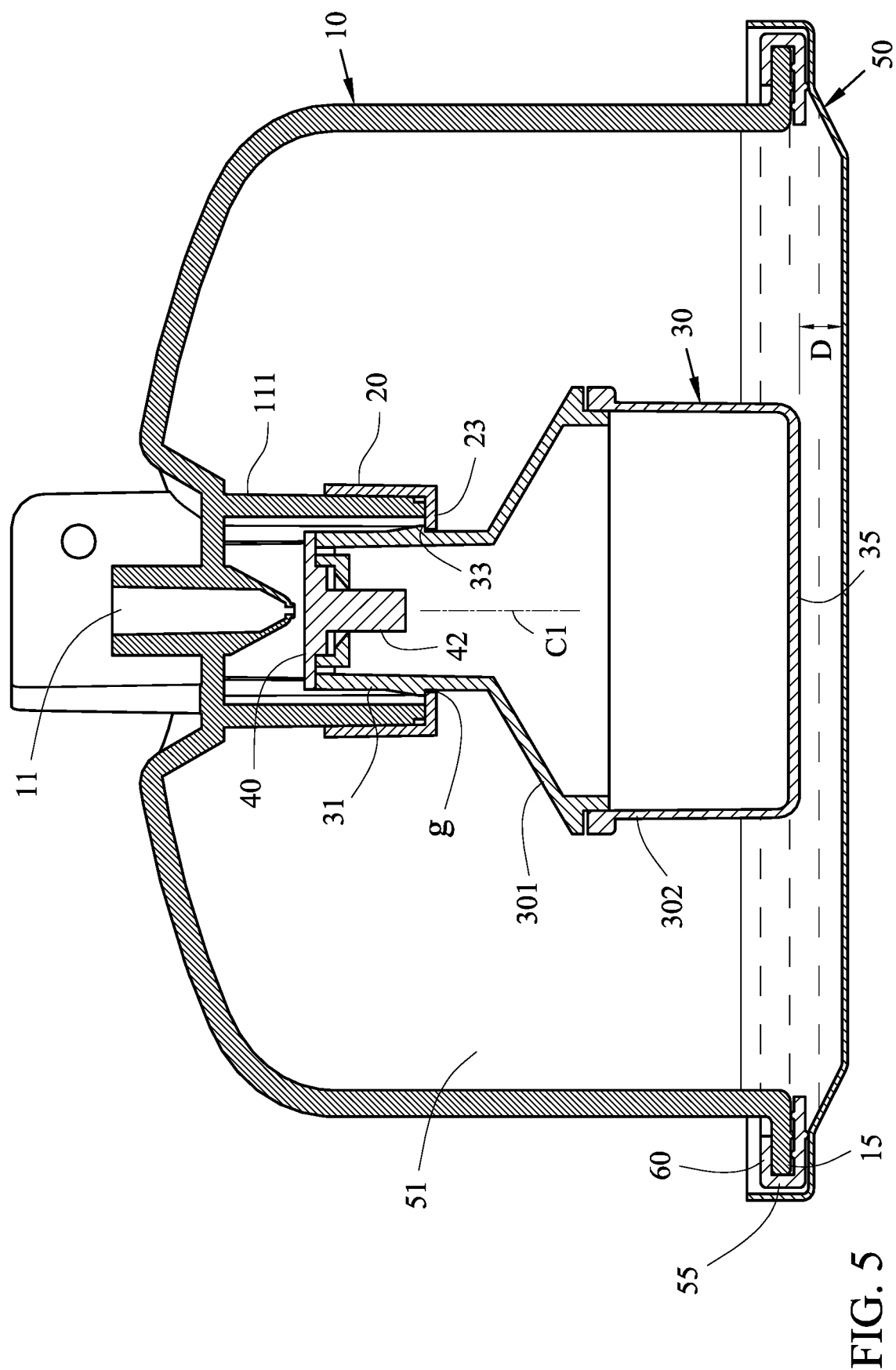
FIG. 5 is a cross-sectional view along a line B-B of FIG. 1.
Figure 6:
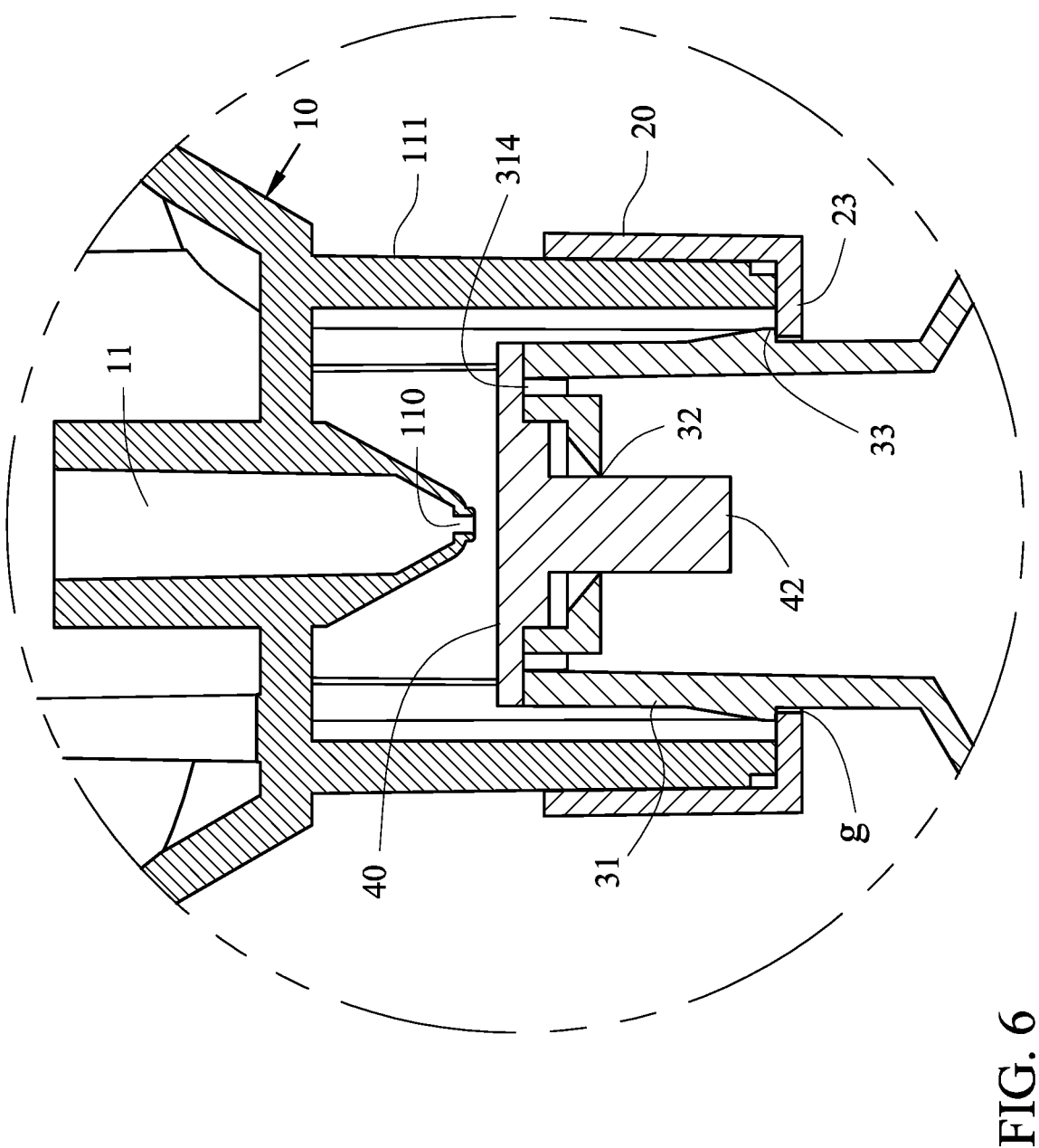
FIG. 6 is a partial enlarged view of the FIG. 5.
Figure 7:
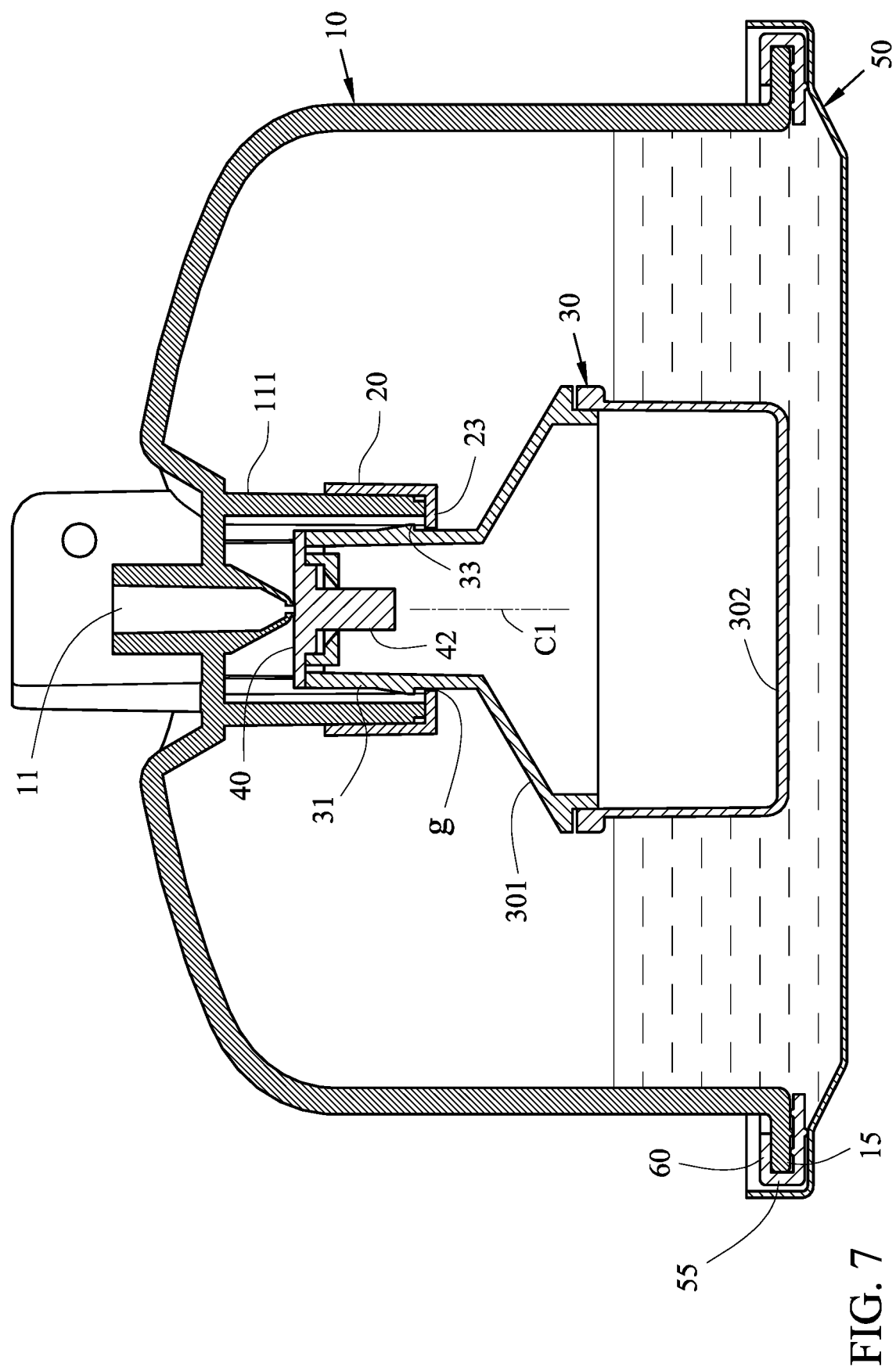
FIG. 7 is an operation diagram illustrating the first embodiment of the invention.
Figure 8:
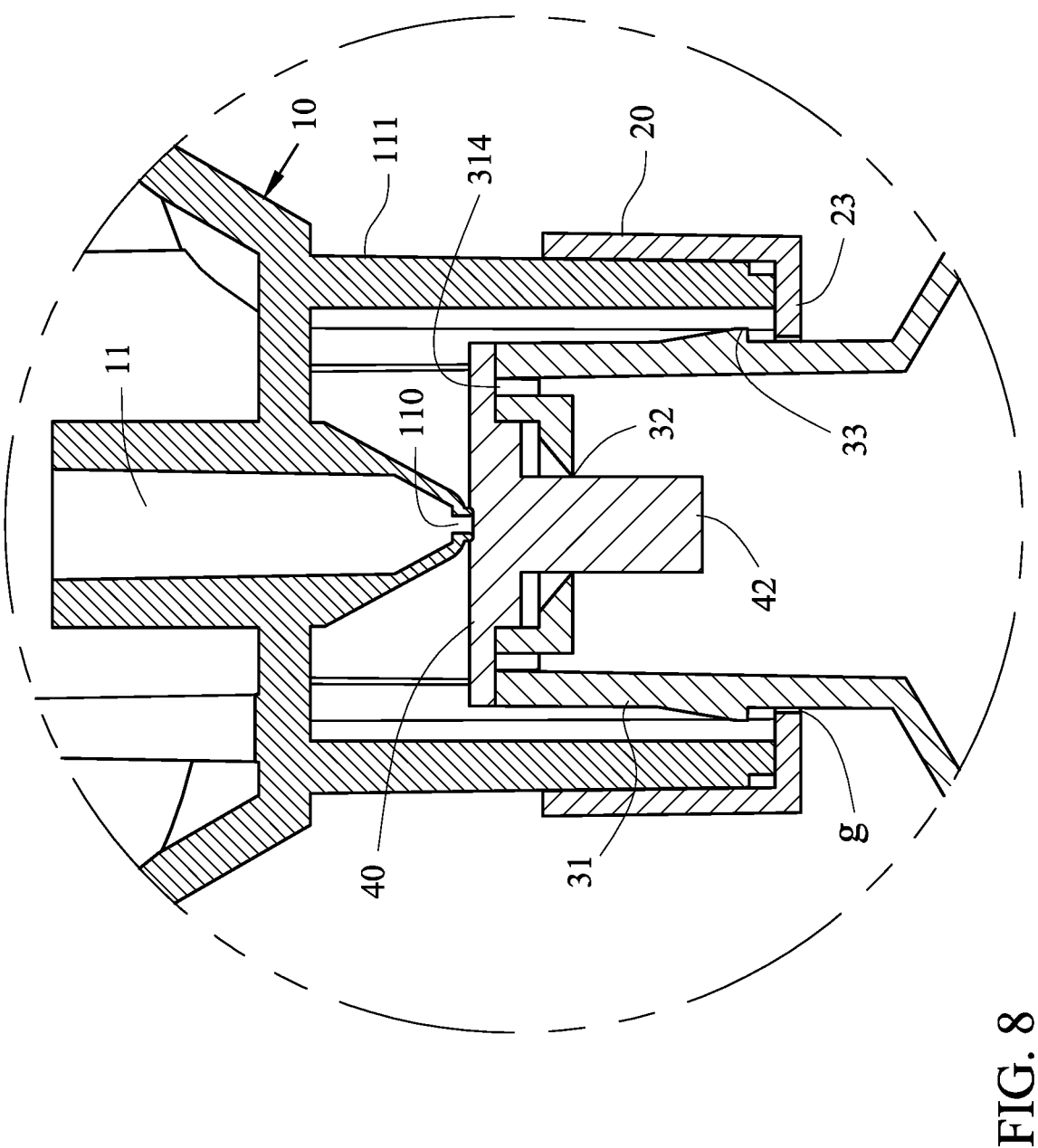
FIG. 8 is a partial enlarged view of the FIG. 7.
Figure 9:
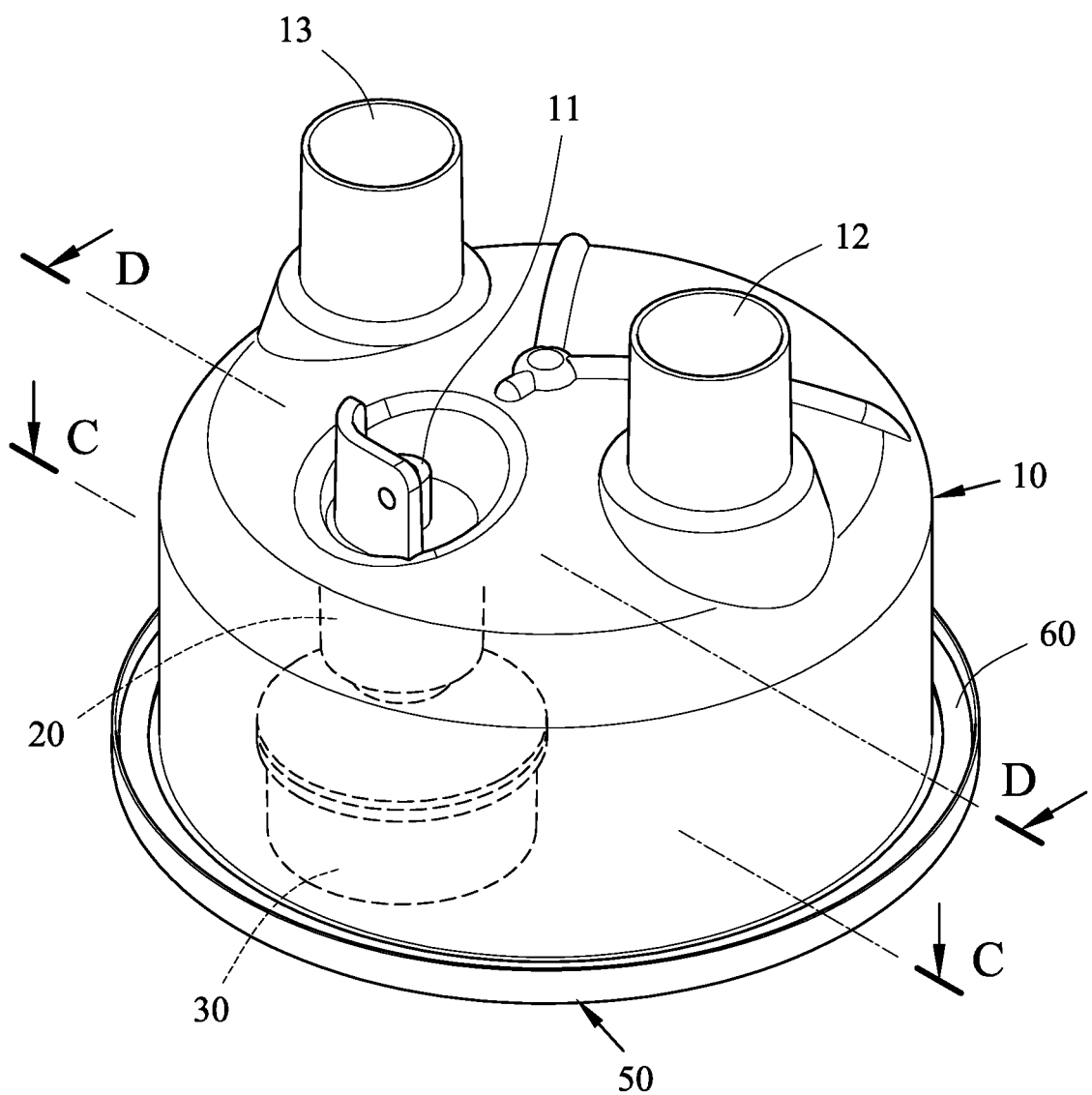
FIG. 9 is a perspective view showing a second preferred embodiment of the invention.
Figure 10:
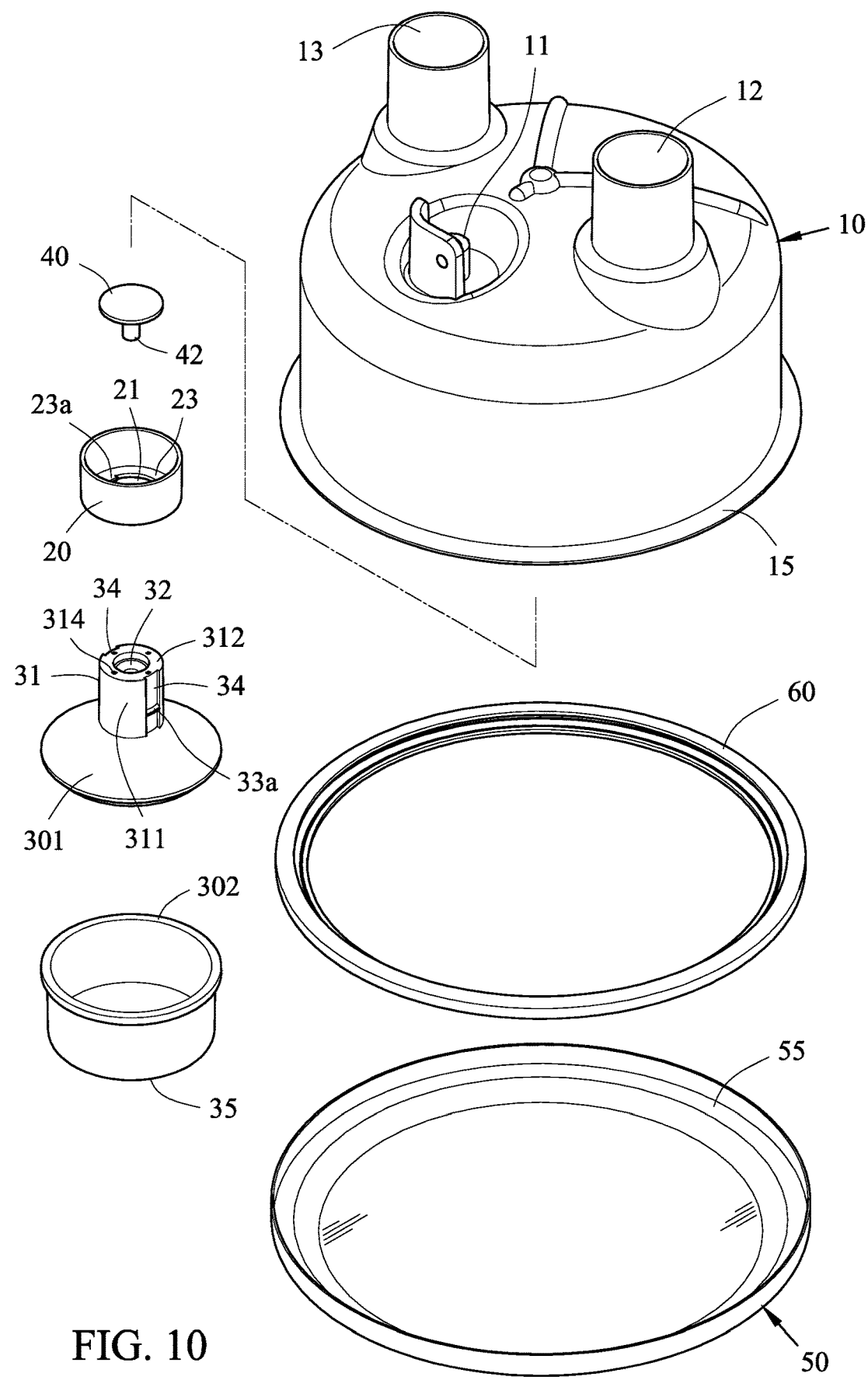
FIG. 10 is an exploded view showing the second preferred embodiment of the invention.
Figure 11:
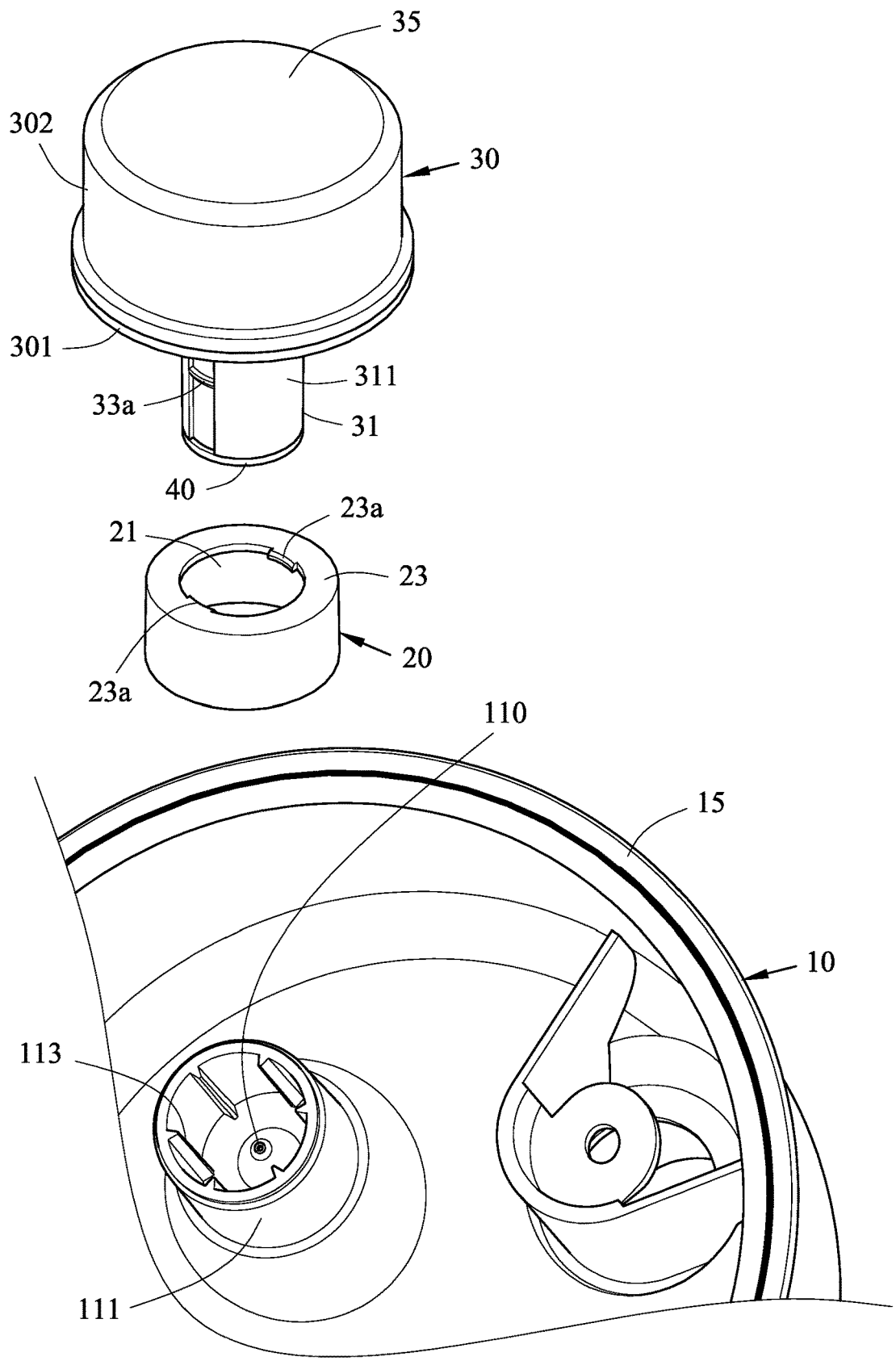
FIG. 11 is a partial exploded view showing the second preferred embodiment of the invention.
Figure 12:
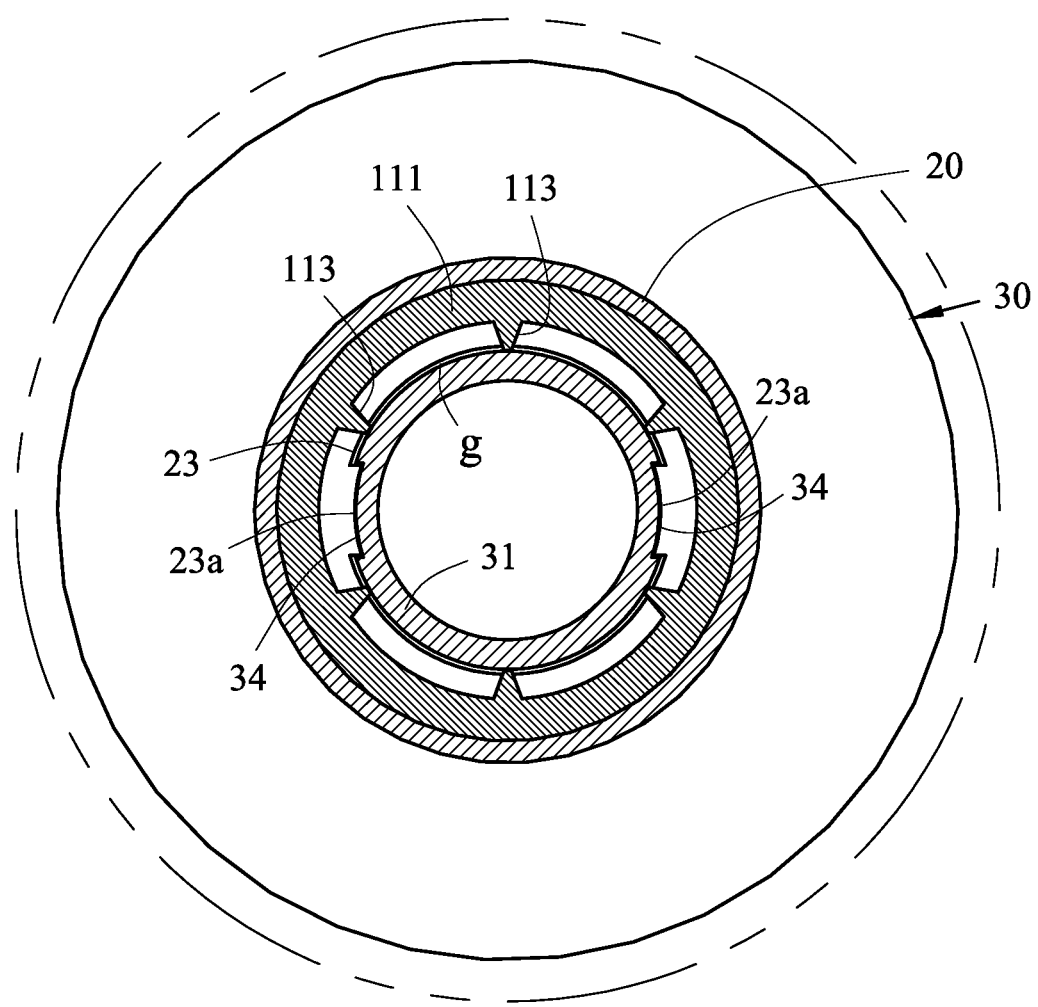
FIG. 12 is a partial cross-sectional perspective view along a line C-C of FIG. 9.

Referring to FIGS. 1 to 8, a humidification chamber in accordance with a first preferred embodiment of the invention comprises a shell body 10, a position limiting element 20, a float 30, a sealing sheet 40 and a heated plate 50; the shell body 10 has a water inlet 11, a gas inlet 12 and a gas outlet 13; the position limiting element 20 has a through hole 21 and an inner edge 23, the position limiting element 20 is fixed on an inside of the water inlet 11; the float 30 has an extending portion 31, a side surface 311 of the extending portion 31 has at least one hook 33, the sealing sheet 40 is configured to be disposed on a top end 312 of the extending portion 31; the heated plate 50 is located below the shell body 10, and the heated plate 50 is used for sealing the shell body 10 to form a chamber space 51; wherein the extending portion 31 is configured to pass through the through hole 21 to enable the hook 33 to be located above the inner edge 23; when the chamber space 51 has no liquid, the hook 33 is stopped on the inner edge 23, the float 30 is configured to be suspended on the position limiting element 20 to enable a distance D is formed between the heated plate 50 and a bottom 35 of the float 30; a liquid is inputted from a water inlet hole 110 of the water inlet 11, when a water level of the chamber space 51 rises the float 30 is configured to rise to comply with the water level increasing; when the sealing sheet 40 contacts the water inlet hole 110 of the water inlet 11, the sealing sheet 40 can block the water inlet hole 110 of the water inlet 11 (as shown in FIG. 7 and FIG. 8); the heated plate 50 can heat the liquid which contained in the chamber space 51, and that therefore provide the moisture; when the gas inlet 12 is used for inputting a gas into the chamber space 51, the gas and the moisture will be mixed into a breathing flow having a suitable humidity, the breathing flow can be output from the gas outlet 13.

Examples of the safety of the first preferred embodiment of the invention will be illustrated below, the water inlet 12 can connect a water storage container (not shown) to replenish the liquid which contained in the chamber space 51; when the liquid of the water storage container is not enough, the water level of the chamber space 51 will significantly fall down, however, the hook 33 can be stopped on the inner edge 23 to enable the float 30 can be suspended on the position limiting element 20 (as shown in FIG. 5 and FIG. 6); even if the chamber space 51 has no liquid at all, the bottom 35 of the float 30 still does not contact the heated plate 50.

Examples of the combination manner of the float 30 and the sealing sheet 40 will be illustrated below, the float 30 has an upper cover 301 and a container 302, the extending portion 31 is located at the upper cover 301, a fixing post 42 of the sealing sheet 40 is configured to be fixed to a fixing hole 32 of the extending portion 31, and therefore the sealing sheet 40 can be disposed on the top end 312 of the extending portion 31.

Examples of the pressure release manner of the float 30 will be illustrated below, the float 30 is a hollow container, the top end 312 of the float 30 is provided with at least one pressure released vent 314, the sealing sheet 40 is appressed on the top end 312 of the float 30, and the pressure released vent 314 is configured to be closed by the sealing sheet 40, and that therefore the sealing sheet 40 can prevent the liquid from infiltrating into the float 30. When the liquid is heated by the heated plate 50, the expansion pressure of the float 30 will be released from the pressure released vent 314. Thus, the sealing sheet 40 can prevent the liquid from infiltrating into the float 30, the sealing sheet 40 can also release the expansion pressure of the float 30.

Examples of the water entering manner of the chamber space 51 will be illustrated below, the side surface 311 of the extending portion 31 has a pair of hooks 33, a distance d1 between outer radial edges of the hooks 33 is larger than a diameter d2 formed by the inner edge 23, a gap g is formed between the inner edge 23 and the extending portion 31. When the liquid is inputted from the water inlet hole 110 of the water inlet 11, the liquid will enter into the chamber space 51 by the gap g.

Examples of the guiding manner of the float 30 will be illustrated below, an inside of the water inlet 11 has an extending tube 111, the position limiting element 20 is configured to be fixed on the extending tube 111 (e.g., close fit), an inner wall of the extending tube 111 has a plurality of guiding ribs 113, and that therefore a center line C1 of the extending portion 31 is configured to be aimed at the water inlet 110 of the water inlet 11, the guiding ribs 113 is configured to guide the movement of the float 30.

Examples of the sealing manner of the heated plate 50 and the shell body 10 will be illustrated below, the shell body 10 has an annular edge 15, the annular edge 15 is sealed with an edge 55 of the heated plate 50, a sealing ring 60 is disposed between the annular edge 15 and the edge 55 of the heated plate 50; wherein the sealing ring 60 is configured to be wrapped on the annular edge 15.

Figure 13:
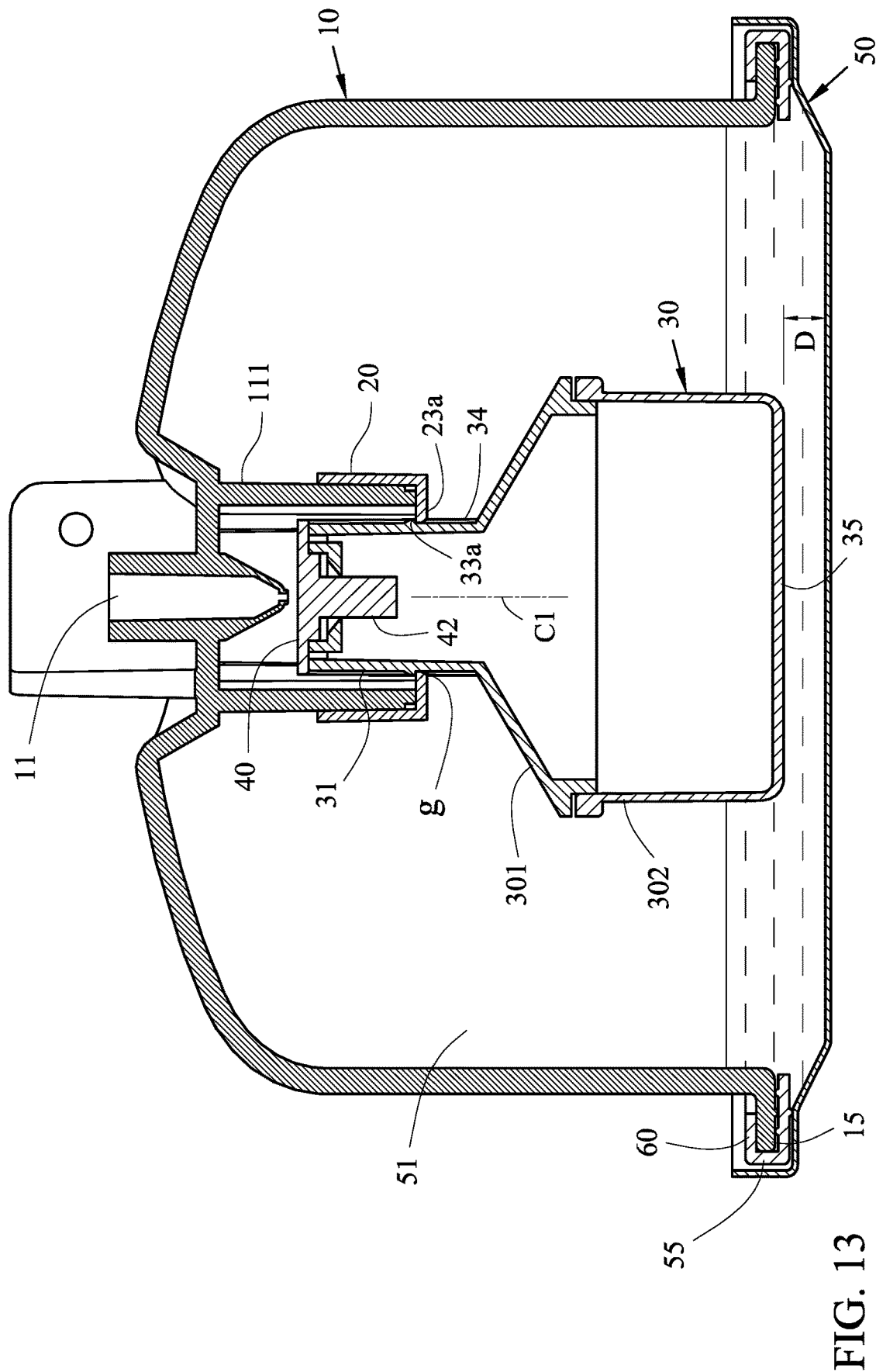
FIG. 13 is a cross-sectional view along a line D-D of FIG. 9.
Figure 14:
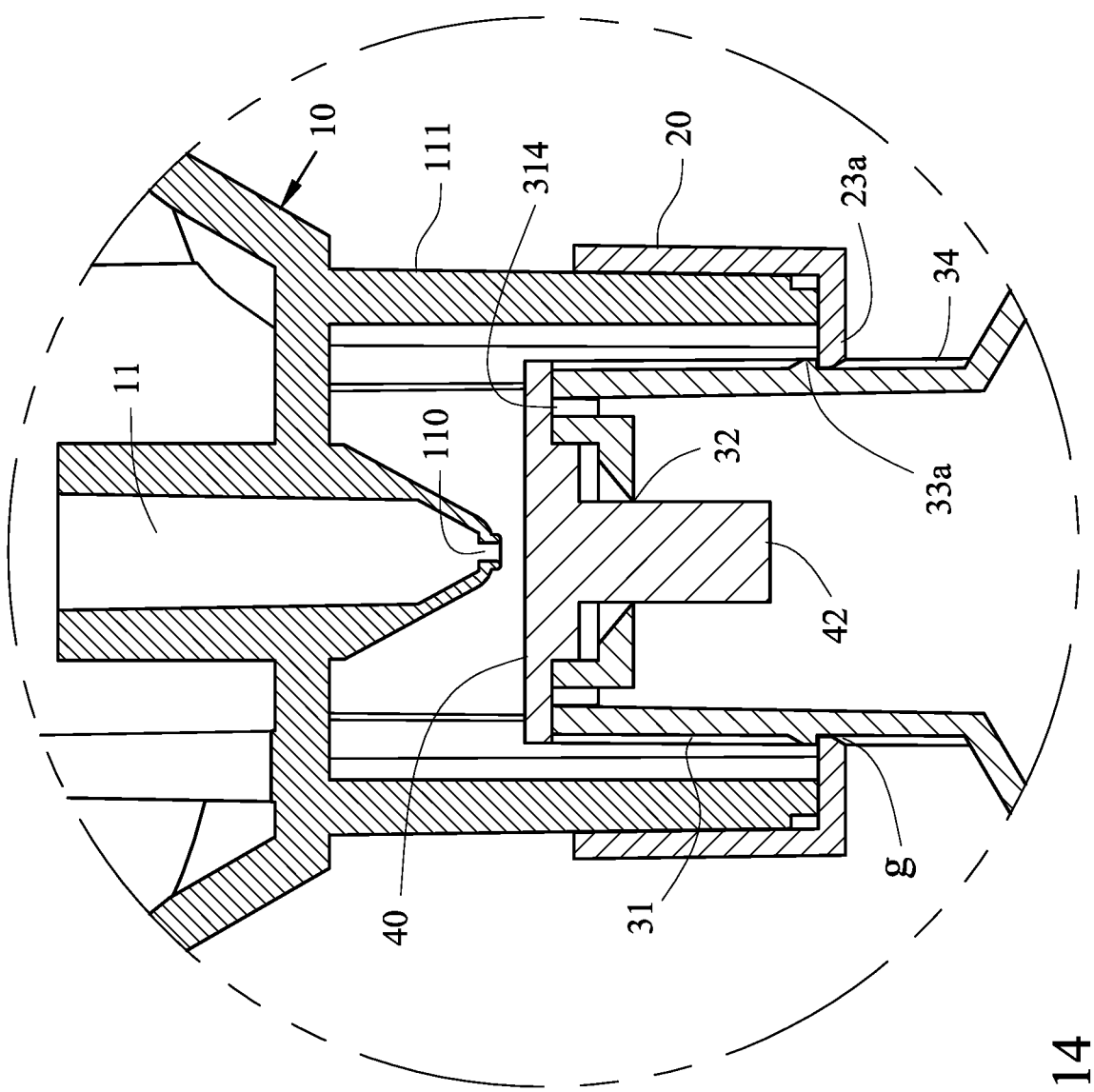
FIG. 14 is a partial enlarged view of the FIG. 13.
Figure 15:
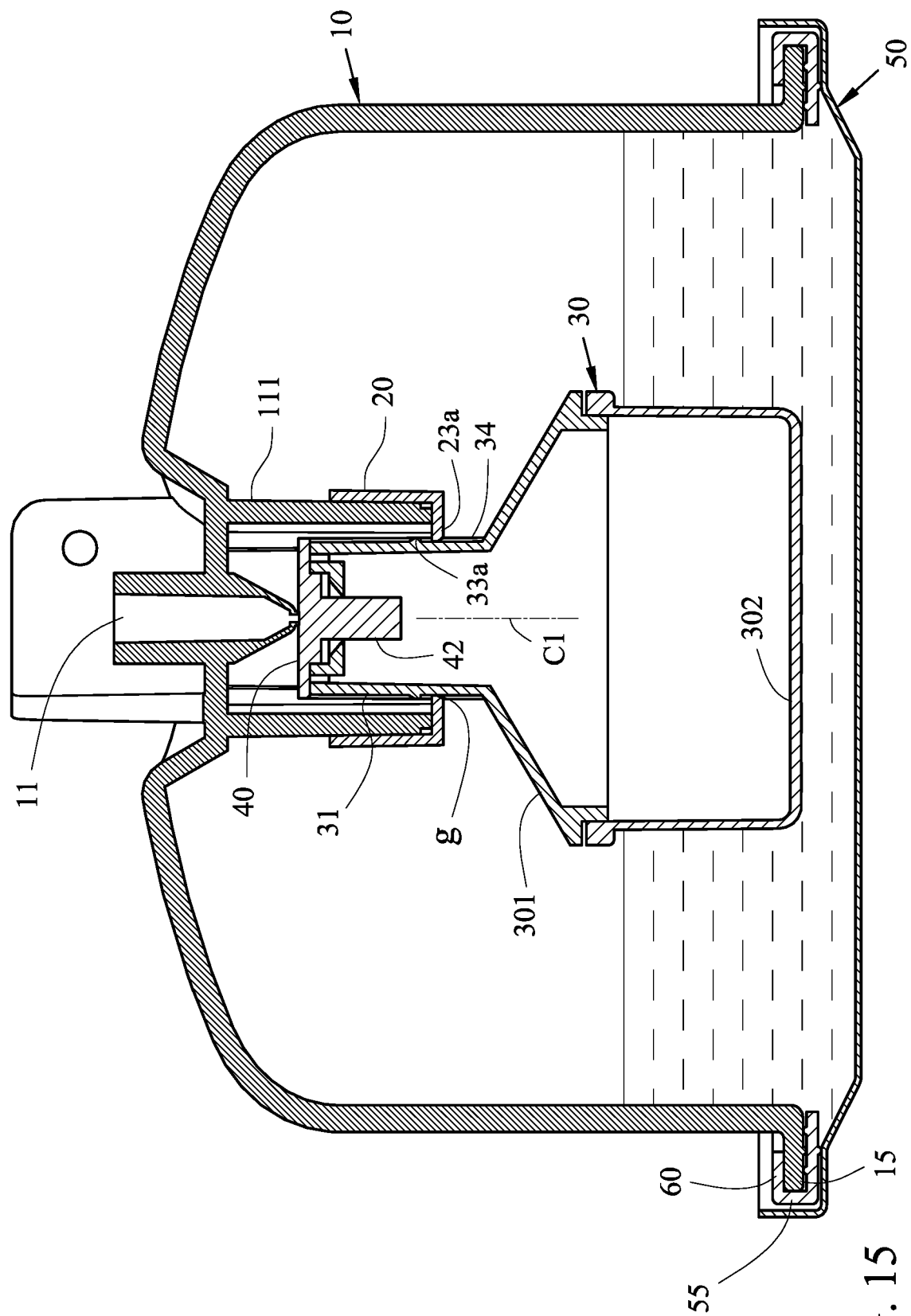
FIG. 15 is an operation diagram illustrating the second embodiment of the invention.
Figure 16:
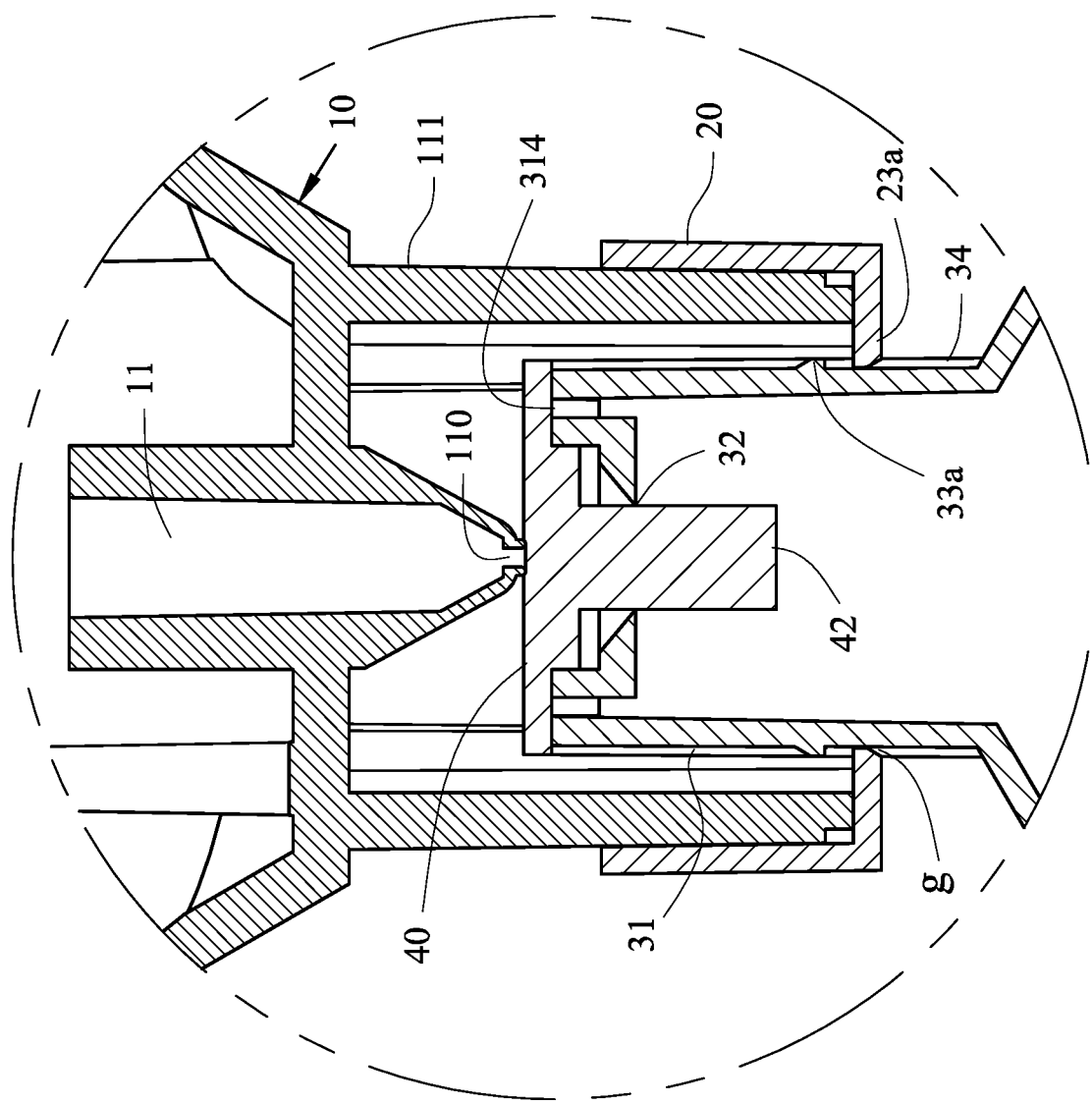
FIG. 16 is a partial enlarged view of the FIG. 15.
Figure 17:
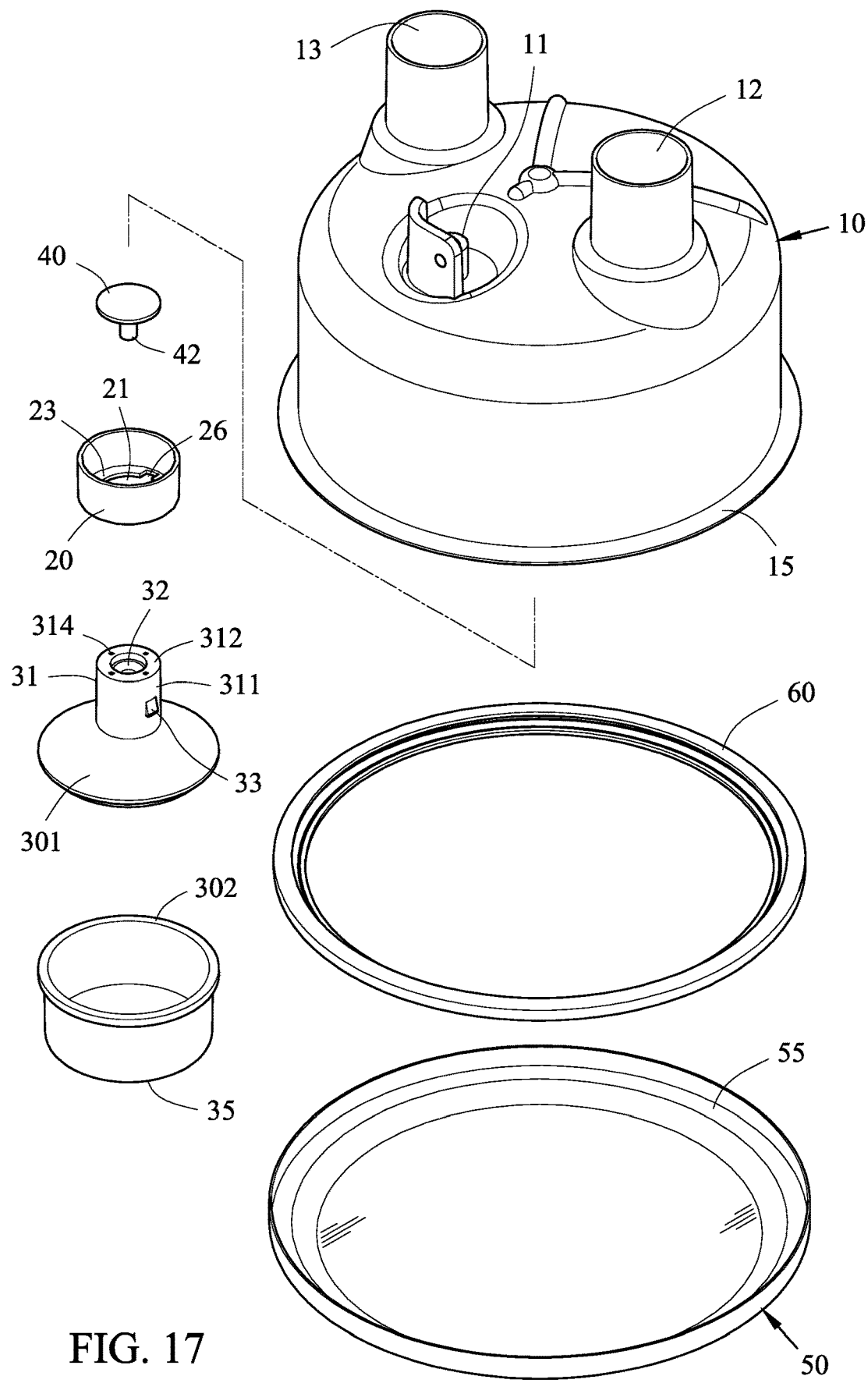
FIG. 17 is an exploded view showing the third preferred embodiment of the invention.

Referring to FIGS. 9 to 16, a humidification chamber in accordance with a second embodiment of the invention comprises a shell body 10, a position limiting element 20, a float 30, a sealing sheet 40 and a heated plate 50; the shell body 10 has a water inlet 11, a gas inlet 12 and a gas outlet 13; the position limiting element 20 has a through hole 21 and an inner edge 23, the position limiting element 20 is fixed on an inside of the water inlet 11, the inner edge 23 has at least one stopper portion 23a; the float 30 has an extending portion 31, a side surface 311 of the extending portion 31 has at least one longitudinal groove 34, the longitudinal groove 34 is provided with a hook 33a, the sealing sheet 40 is configured to be disposed on a top end 312 of the extending portion 31; the heated plate 50 is located below the shell body 10, and the heated plate 50 is used for sealing the shell body 10 to form a chamber space 51; wherein the extending portion 31 is configured to pass through the through hole 21 to enable the stopper portion 23a to be located within the longitudinal groove 34, and the hook 33a is located above the stopper portion 23a; when the chamber space 51 has no liquid, the hook 33a is stopped on the stopper portion 23a, the float 30 is configured to be suspended on the position limiting element 20 to enable a distance D is formed between the heated plate 50 and a bottom 35 of the float 30; a liquid is inputted from a water inlet hole 110 of the water inlet 11, when a water level of the chamber space 51 rises the float 30 is configured to rise to comply with the water level increasing; when the sealing sheet 40 contacts the water inlet hole 110 of the water inlet 11, the sealing sheet 40 can block the water inlet hole 110 of the water inlet 11 (as shown in FIG. 15 and FIG. 16); the heated plate 50 can heat the liquid which contained in the chamber space 51, and that therefore provide the moisture; when the gas inlet 12 is used for inputting a gas into the chamber space 51, the gas and the moisture will be mixed into a breathing flow having a suitable humidity, the breathing flow can be output from the gas outlet 13.

Examples of the safety of the second embodiment of the invention will be illustrated below, the water inlet 12 can connect a water storage container (not shown) to replenish the liquid which contained in the chamber space 51; when the liquid of the water storage container is not enough, the water level of the chamber space 51 will significantly fall down, however, the hook 33a can be stopped on the stopper portion 23a to enable the float 30 can be suspended on the position limiting element 20 (as shown in FIG. 13 and FIG. 14); even if the chamber space 51 has no liquid at all, a bottom 35 of the float 30 still does not contact the heated plate 50.

Examples of the combination manner of the float 30 and the sealing sheet 40 will be illustrated below, the float 30 has an upper cover 301 and a container 302, the extending portion 31 is located at the upper cover 301, a fixing post 42 of the sealing sheet 40 is configured to be fixed to a fixing hole 32 of the extending portion 31, and therefore the sealing sheet 40 is configured to be disposed on the top end 312 of the extending portion 31.

Examples of the pressure release manner of the float 30 will be illustrated below, the float 30 is a hollow container, the top end 312 of the float 30 is provided with at least one pressure released vent 314, the sealing sheet 40 is appressed on the top end 312 of the float 30, and the pressure released vent 314 is configured to be closed by the sealing sheet 40, and that therefore the sealing sheet 40 can prevent the liquid from infiltrating into the float 30. When the liquid is heated by the heated plate 50, the expansion pressure of the float 30 will be released from the pressure released vent 314. Thus, the sealing sheet 40 can prevent the liquid from infiltrating into the float 30, the sealing sheet 40 can also release the expansion pressure of the float 30.

Examples of the water entering manner of the chamber space 51 will be illustrated below, the side surface 311 of the extending portion 31 has a pair of longitudinal grooves 34 and a pair of hooks 33a, a gap g is formed between the inner edge 23 and the extending portion 31. When the liquid is inputted from the water inlet hole 110 of the water inlet 11, the liquid will enter into the chamber space 51 by the gap g.

Examples of the guiding manner of the float 30 will be illustrated below, an inside of the water inlet 11 has an extending tube 111, the position limiting element 20 is configured to be fixed on the extending tube 111 (e.g., close fit), an inner wall of the extending tube 111 has a plurality of guiding ribs 113, and that therefore a center line C1 of the extending portion 31 is configured to be aimed at the water inlet 110 of the water inlet 11, the guiding ribs 113 is configured to guide the movement of the float 30.

Figure 18:
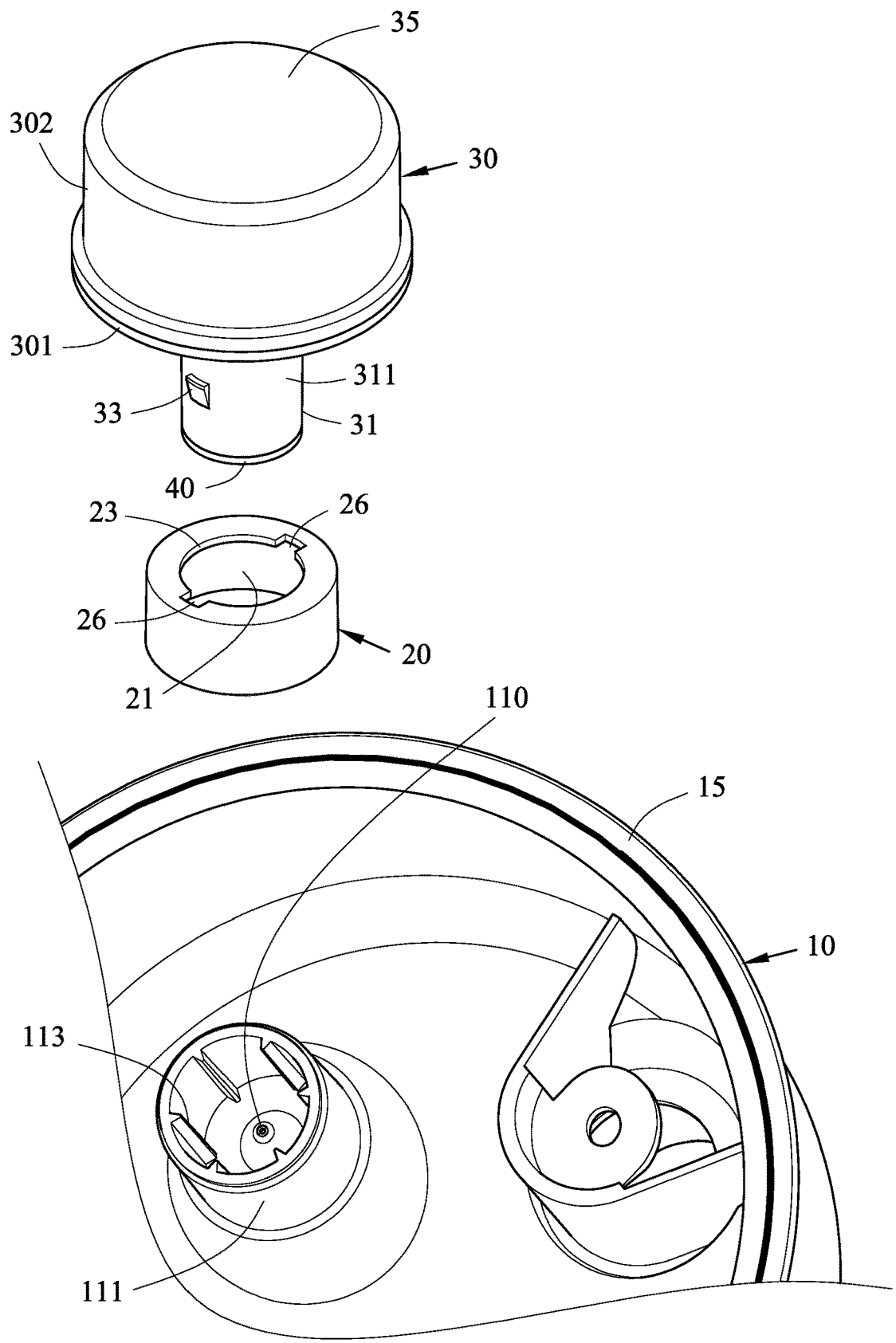
FIG. 18 is a partial exploded view showing the third preferred embodiment of the invention.
Figure 19:
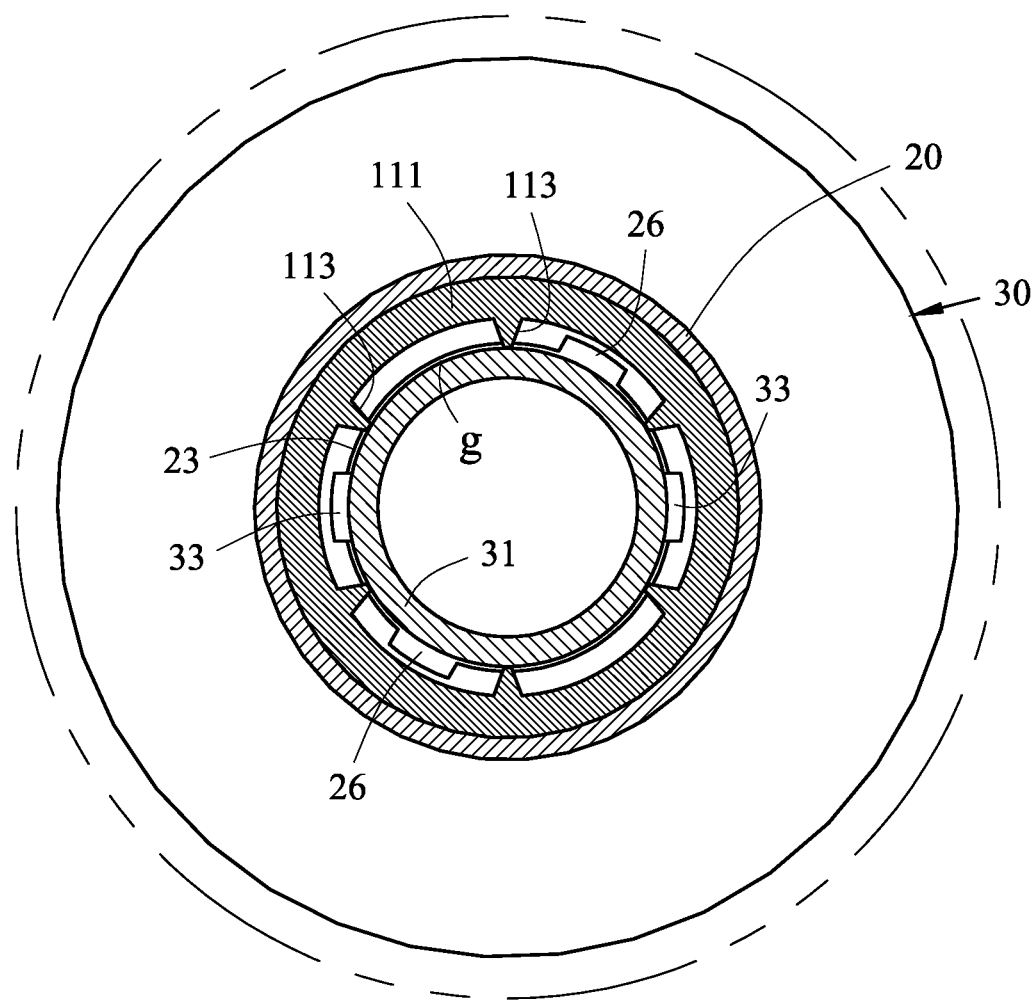
FIG. 19 is a partial cross-sectional perspective diagram illustrating the third preferred embodiment of the invention.
Figure 20:
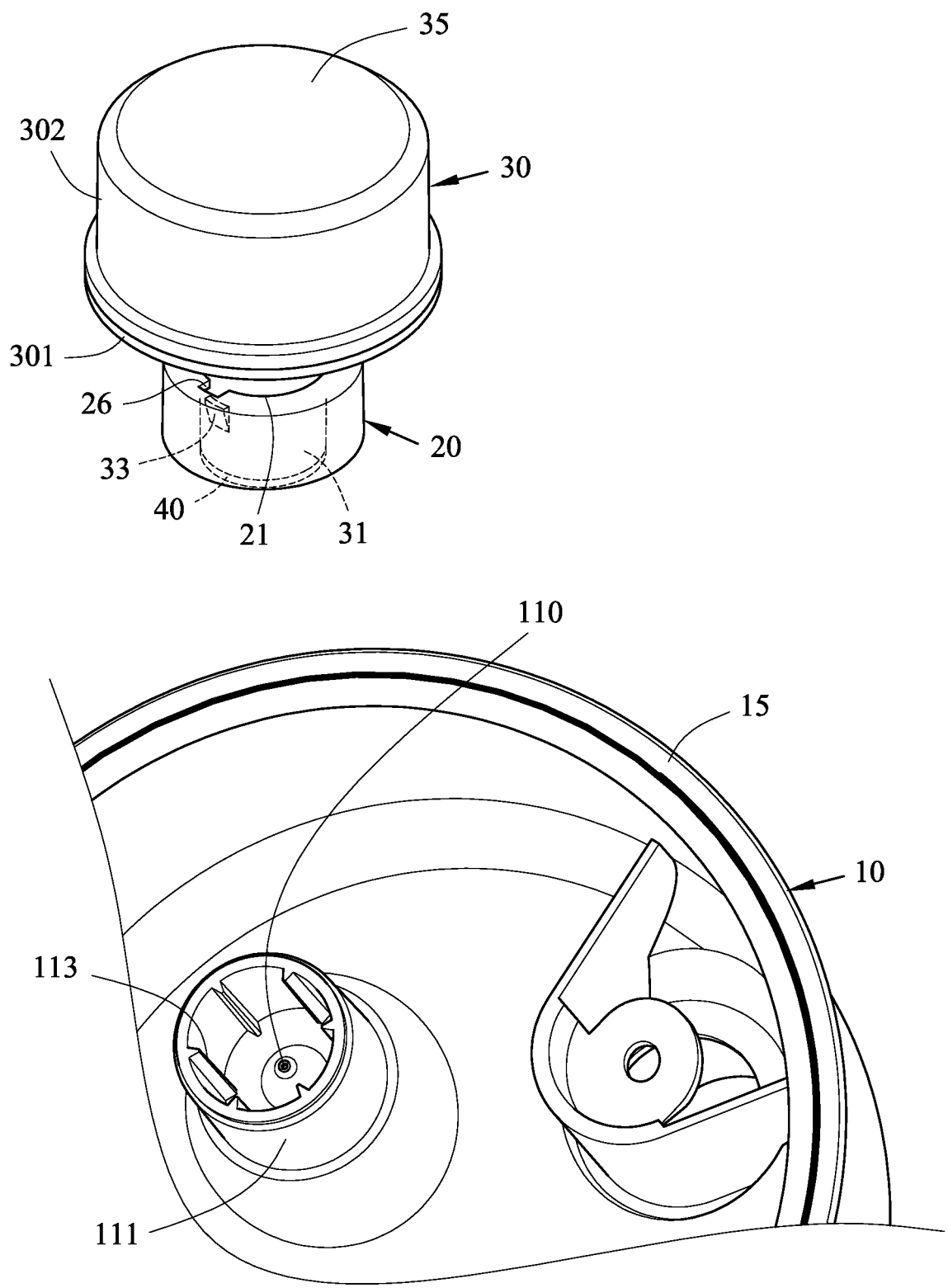
FIG. 20 is a diagram illustrating the hook is passed through the notch.
Figure 21:
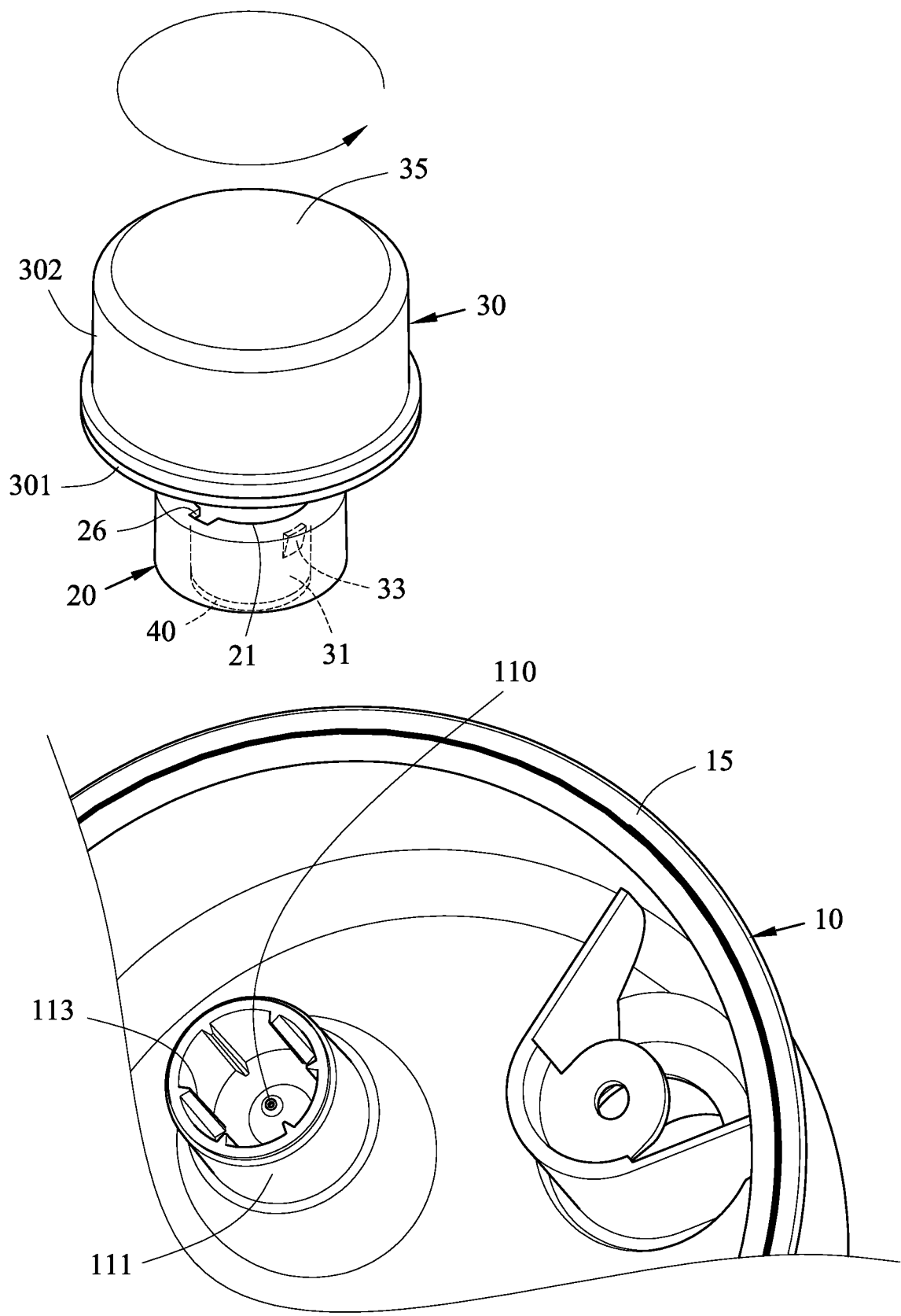
FIG. 21 is a diagram illustrating the float is rotated to an angle.

Referring to FIG. 1, FIGS. 5 to 8, FIGS. 17 to 21, a humidification chamber in accordance with a third preferred embodiment of the invention comprises a shell body 10, a position limiting element 20, a float 30, a sealing sheet 40 and a heated plate 50; the shell body 10 has a water inlet 11, a gas inlet 12 and a gas outlet 13, an inside of the water inlet 11 has an extending tube 111, an inner wall of the extending tube 111 has a plurality of guiding ribs 113; the position limiting element 20 has a through hole 21 and an inner edge 23, the inner edge 23 is provided with at least one notch 26; the float 30 has an extending portion 31, a side surface 311 of the extending portion 31 has at least one hook 33, the sealing sheet 40 is configured to be disposed on a top end 312 of the extending portion 31; the heated plate 50 is located below the shell body 10, and the heated plate 50 is used for sealing the shell body 10 to form a chamber space 51; wherein the extending portion 31 is configured to pass through the through hole 21, the hook 33 is configured to pass through the notch 26 (as shown in FIG. 18 and FIG. 20), and the float 30 can be rotated to an angle to enable the hook 33 to be located at an inside of the inner edge 23 (as shown in FIG. 20 and FIG. 21); the position limiting element 20 is configured to be fixed on the extending tube 111, therefore the hook 33 and the notch 26 is configured to be separated by the guiding ribs 113 of the extending tube 111 (as shown in FIG. 19); when the chamber space 51 has no liquid, the hook 33 is stopped on the inner edge 23, the float 30 is configured to be suspended on the position limiting element 20 to enable a distance D is formed between the heated plate 50 and a bottom 35 of the float 30; when a liquid is inputted from a water inlet hole 110 of the water inlet 11, the water level of the chamber space 51 will rise to enable the float 30 rises to comply with the water level increasing; when the sealing sheet 40 contacts the water inlet hole 110 of the water inlet 11, the sealing sheet 40 can block the water inlet hole 110 of the water inlet 11 (as shown in FIG. 7 and FIG. 8); the heated plate 50 can heat the liquid which contained in the chamber space 51, and that therefore provide the moisture; when the gas inlet 12 is used for inputting a gas into the chamber space 51, the gas and the moisture will be mixed into a breathing flow having a suitable humidity, the breathing flow can be output from the gas outlet 13.

Examples of the water entering manner of the chamber space 51 will be illustrated below, a gap g is formed between the inner edge 23 and the extending portion 31. When a liquid is inputted from the water inlet hole 110 of the water inlet 11, the liquid will enter into the chamber space 51 by the gap g and the notch 26.

What is claimed is:

1. A humidification chamber having suspension type float, the humidification chamber comprising:
    a shell body (10), the shell body (10) has a water inlet (11), a gas inlet (12) and a gas outlet (13);
    a position limiting element (20), the position limiting element (20) has a through hole (21) and an inner edge (23), the position limiting element (20) is fixed on an inside of the water inlet (11);
    a float (30) having an extending portion (31), a side surface (311) of the extending portion (31) has at least one hook (33);
    a sealing sheet (40), the sealing sheet (40) is configured to be disposed on a top end (312) of the extending portion (31); and
    a heated plate (50), the heated plate (50) is located below the shell body (10), and the heated plate (50) is used for sealing the shell body (10) to form a chamber space (51);
    wherein the extending portion (31) is configured to pass through the through hole (21) to enable the hook (33) to be located above the inner edge (23); a water inlet hole (110) of the water inlet (11) is configured for inputting a liquid, when a water level of the chamber space (51) rises the float (30) is configured to rise to comply with the water level increasing; when the water inlet hole (110) of the water inlet (11) is contacted with the sealing sheet (40), the water inlet hole (110) of the water inlet (11) is configured to be blocked by the sealing sheet (40); when the hook (33) is stopped on the inner edge (23), the float (30) is configured to be suspended on the position limiting element (20), and that therefore a distance (D) is formed between the heated plate (50) and a bottom (35) of the float (30).

2. The humidification chamber having suspension type float of claim 1, wherein the float (30) has an upper cover (301) and a container (302), the extending portion (31) is located at the upper cover (301), a fixing post (42) of the sealing sheet (40) is configured to be fixed to a fixing hole (32) of the extending portion (31).

3. The humidification chamber having suspension type float of claim 1, wherein the float (30) is a hollow container, the top end (312) of the float (30) is provided with at least one pressure released vent (314), the sealing sheet (40) is appressed on the top end (312) of the float (30), and the pressure released vent (314) is configured to be closed by the sealing sheet (40), and that therefore the sealing sheet (40) can prevent the liquid from infiltrating into the float (30); when the liquid is heated by the heated plate (50), the expansion pressure of the float (30) will be released from the pressure released vent (314).

4. The humidification chamber having suspension type float of claim 1, wherein the side surface (311) of the extending portion (31) has a pair of hooks (33), a distance (d1) between outer radial edges of the hooks (33) is larger than a diameter (d2) formed by the inner edge (23), a gap (g) is formed between the inner edge (23) and the extending portion (31); when the liquid is inputted from the water inlet hole (110) of the water inlet (11), the liquid will enter into the chamber space (51) by the gap (g).

5. The humidification chamber having suspension type float of claim 1, wherein an inside of the water inlet (11) has an extending tube (111), the position limiting element (20) is configured to be fixed on the extending tube (111), an inner wall of the extending tube (111) has a plurality of guiding ribs (113), and that therefore a center line (C1) of the extending portion (31) is configured to be aimed at the water inlet (110) of the water inlet (11), the guiding ribs (113) are configured to guide the movement of the float (30).

6. A humidification chamber having suspension type float, the humidification chamber comprising:
- a shell body (10), the shell body (10) has a water inlet (11), a gas inlet (12) and a gas outlet (13);
- a position limiting element (20), the position limiting element (20) has a through hole (21) and an inner edge (23), the position limiting element (20) is fixed on an inside of the water inlet (11), the inner edge (23) has at least one stopper portion (23a);
- a float (30) having an extending portion (31), a side surface (311) of the extending portion (31) has at least one longitudinal groove (34), the longitudinal groove (34) is provided with a hook (33a)
- a sealing sheet (40), the sealing sheet (40) is configured to be disposed on a top end (312) of the extending portion (31); and
- a heated plate (50), the heated plate (50) is located below the shell body (10), and the heated plate (50) is used for sealing the shell body (10) to form a chamber space (51);
- wherein the extending portion (31) is configured to pass through the through hole (21) to enable the stopper portion (23a) to be located within the longitudinal groove (34), and the hook (33a) is located above the stopper portion (23a); a water inlet hole (110) of the water inlet (11) is configured for inputting a liquid, when a water level of the chamber space (51) rises the float (30) is configured to rise to comply with the water level increasing; when the water inlet hole (110) of the water inlet (11) is contacted with the sealing sheet (40), the water inlet hole (110) of the water inlet (11) is configured to be blocked by the sealing sheet (40); when the hook (33a) is stopped on the stopper portion (23a), the float (30) is configured to be suspended on the position limiting element (20), and that therefore a distance (D) is formed between the heated plate (50) and a bottom (35) of the float (30).

7. The humidification chamber having suspension type float of claim 6, wherein the float (30) has an upper cover (301) and a container (302), the extending portion (31) is located at the upper cover (301), a fixing post (42) of the sealing sheet (40) is configured to be fixed to a fixing hole (32) of the extending portion (31).

8. The humidification chamber having suspension type float of claim 6, wherein the float (30) is a hollow container, the top end (312) of the float (30) is provided with at least one pressure released vent (314), the sealing sheet (40) is appressed on the top end (312) of the float (30), and the pressure released vent (314) is configured to be closed by the sealing sheet (40), and that therefore the sealing sheet (40) can prevent the liquid from infiltrating into the float (30); when the liquid is heated by the heated plate (50), the expansion pressure of the float (30) will be released from the pressure released vent (314).

9. The humidification chamber having suspension type float of claim 6, wherein the side surface (311) of the extending portion (31) has a pair of longitudinal grooves (34) and a pair of hooks (33), a gap (g) is formed between the inner edge (23) and the extending portion (31); when the liquid is inputted from the water inlet hole (110) of the water inlet (11), the liquid will enter into the chamber space (51) by the gap (g).

10. The humidification chamber having suspension type float of claim 6, wherein an inside of the water inlet (11) has an extending tube (111), the position limiting element (20) is configured to be fixed on the extending tube (111), an inner wall of the extending tube (111) has a plurality of guiding ribs (113), and that therefore a center line (C1) of the extending portion (31) is configured to be aimed at the water inlet (110) of the water inlet (11), the guiding ribs (113) are configured to guide the movement of the float (30).

11. A humidification chamber having suspension type float, the humidification chamber comprising:
- a shell body (10), the shell body (10) has a water inlet (11), a gas inlet (12) and a gas outlet (13), an inside of the water inlet (11) has an extending tube (111), an inner wall of the extending tube (111) has a plurality of guiding ribs (113);
- a position limiting element (20), the position limiting element (20) has a through hole (21) and an inner edge (23), the inner edge (23) is provided with at least one notch (26);
- a float (30) having an extending portion (31), a side surface (311) of the extending portion (31) has at least one hook (33);
- a sealing sheet (40), the sealing sheet (40) is configured to be disposed on a top end (312) of the extending portion (31); and
- a heated plate (50), the heated plate (50) is located below the shell body (10), and the heated plate (50) is used for sealing the shell body (10) to form a chamber space (51);
- wherein the extending portion (31) is configured to pass through the through hole (21), the hook (33) is configured to pass through the notch (26), and the float (30) can be rotated to an angle to enable the hook (33) to be located at an inside of the inner edge (23); the position limiting element (20) is configured to be fixed on the extending tube (111), therefore the hook (33) and the notch (26) are configured to be separated by the guiding ribs (113) of the extending tube (111); when a water inlet hole (110) of the water inlet (11) is contacted with the sealing sheet (40), the water inlet hole (110) of the water inlet (11) is configured to be blocked by the sealing sheet (40); when the hook (33) is stopped on the inner edge (23), the float (30) is configured to be suspended on the position limiting element (20), and that therefore a distance (D) is formed between the heated plate (50) and a bottom (35) of the float (30).

12. The humidification chamber having suspension type float of claim 11, wherein the float (30) has an upper cover (301) and a container (302), the extending portion (31) is located at the upper cover (301), a fixing post (42) of the sealing sheet (40) is configured to be fixed to a fixing hole (32) of the extending portion (31).

13. The humidification chamber having suspension type float of claim 11, wherein the float (30) is a hollow container, the top end (312) of the float (30) is provided with at least one pressure released vent (314), the sealing sheet (40) is appressed on the top end (312) of the float (30), and the pressure released vent (314) is configured to be closed by the sealing sheet (40), and that therefore the sealing sheet (40) can prevent liquid from infiltrating into the float (30); when the liquid is heated by the heated plate (50), the expansion pressure of the float (30) will be released from the pressure released vent (314).

14. The humidification chamber having suspension type float of claim 11, wherein a gap (g) is formed between the inner edge (23) and the extending portion (31); when liquid is inputted from the water inlet hole (110) of the water inlet (11), the liquid will enter into the chamber space (51) by the gap (g) and the notch (26).

15. The humidification chamber having suspension type float of claim 11, wherein the shell body (10) has an annular edge (15), the annular edge (15) is sealed with an edge (55) of the heated plate (50), a sealing ring (60) is disposed between the annular edge (15) and the edge (55) of the heated plate (50), the sealing ring (60) is configured to be wrapped on the annular edge (15).

* * * * *